(12) United States Patent
Zhou

(10) Patent No.: US 11,707,538 B2
(45) Date of Patent: *Jul. 25, 2023

(54) METHODS AND DEVICES TO GENERATE [F-18]TRIFLYL FLUORIDE AND OTHER [F-18] SULFONYL FLUORIDES

(71) Applicant: Dong Zhou, St. Louis, MO (US)

(72) Inventor: Dong Zhou, St. Louis, MO (US)

(73) Assignee: Washington University, St. Louis, MO (US)

( * ) Notice: Subject to any disclaimer, the term of this patent is extended or adjusted under 35 U.S.C. 154(b) by 226 days.

This patent is subject to a terminal disclaimer.

(21) Appl. No.: 17/150,186

(22) Filed: Jan. 15, 2021

(65) Prior Publication Data

US 2021/0236659 A1 Aug. 5, 2021

Related U.S. Application Data

(63) Continuation-in-part of application No. 15/403,954, filed on Jan. 11, 2017, now Pat. No. 11,242,314.

(60) Provisional application No. 62/961,521, filed on Jan. 15, 2020, provisional application No. 62/277,222, filed on Jan. 11, 2016.

(51) Int. Cl.

| | | |
|---|---|---|
| *A61K 49/04* | (2006.01) | |
| *C07C 315/04* | (2006.01) | |
| *C07C 315/06* | (2006.01) | |
| *C07C 311/48* | (2006.01) | |
| *C07D 487/06* | (2006.01) | |
| *C07D 401/12* | (2006.01) | |
| *C07H 3/08* | (2006.01) | |
| *C07C 67/317* | (2006.01) | |
| *C07C 67/307* | (2006.01) | |
| *C07B 39/00* | (2006.01) | |
| *C07B 59/00* | (2006.01) | |
| *B01J 23/92* | (2006.01) | |
| *B01J 27/232* | (2006.01) | |
| *B01J 31/02* | (2006.01) | |

(52) U.S. Cl.
CPC .......... *A61K 49/0433* (2013.01); *B01J 23/92* (2013.01); *B01J 27/232* (2013.01); *B01J 31/0237* (2013.01); *C07B 39/00* (2013.01); *C07B 59/001* (2013.01); *C07C 67/307* (2013.01); *C07C 67/317* (2013.01); *C07C 311/48* (2013.01); *C07C 315/04* (2013.01); *C07C 315/06* (2013.01); *C07D 401/12* (2013.01); *C07D 487/06* (2013.01); *C07H 3/08* (2013.01); *C07B 2200/05* (2013.01); *C07C 2602/10* (2017.05)

(58) Field of Classification Search
None
See application file for complete search history.

(56) References Cited

U.S. PATENT DOCUMENTS

| | | | |
|---|---|---|---|
| 7,744,851 B2 | 6/2010 | DiMagno et al. | |
| 8,206,593 B2 | 6/2012 | Lee et al. | |
| 2008/0281090 A1* | 11/2008 | Lee .................. | B01J 19/0093 422/600 |
| 2011/0006011 A1 | 1/2011 | Aerts et al. | |
| 2012/0283490 A1 | 11/2012 | Gangadharmath et al. | |
| 2013/0005956 A1 | 1/2013 | Gangadharmath et al. | |
| 2014/0039074 A1 | 2/2014 | Chi et al. | |
| 2015/0232392 A1 | 8/2015 | Chi et al. | |
| 2017/0197912 A1* | 7/2017 | Zhou .................. | C07B 59/002 |

FOREIGN PATENT DOCUMENTS

| | | |
|---|---|---|
| WO | 2011141410 A1 | 11/2011 |
| WO | 2015143019 A2 | 9/2015 |

OTHER PUBLICATIONS

Heylin, M., et al., "Chemistry grads post gains in 2006 ", Chemical and Engineering News , pp. 43-52 (Year: 2004).*
Zhou, D., et al., "Sulfonyl [18F]fluorides open new landscape for radiofluorination", JNM, pp. 1-5 (Year: 2017).*
Inkster, J.A., et al., "Sulfonyl Fluoride-Based Prosthetic Compounds as Potential18F Labelling Agents", Chemistry, pp. 11079-11087 (Year: 2012).*
Aerts et al., "Fast production of highly concentrated reactive [18F] fluoride for aliphatic and aromatic nucleophilic radiolabelling," Tetrahedron Lett., Jan. 6, 2010, pp. 64-66, vol. 51, No. 1, Elsevier Ltd.
Beyerlein et al., "Automated synthesis and purification of [18F] fluoro-[di-deutero]methyl tosylate," J. Label. Compd. Radiopharm., Jun. 15, 2013, pp. 360-363, vol. 56, No. 7, John Wiley & Sons, Ltd.
Borders et al., "Synthesis of Sulfonyl Fluorides by Use of a Fluoride Ion Exchange Resin", J. Org. Chem., 1972, pp. 3549-3550.
Cai et al., "Chemistry with [18F]Fluoride Ion," Eur. J. Org. Chem., Jun. 2008, pp. 2853-2873, vol. 2008, No. 17, Wiley-VCH Verlag GmbH & Co. KGaA, Weinheim.
Jong et al., "Sulfur(VI) Fluoride Exchange (SuFEx): Another Good Reaction for Click Chemistry," Angew. Chem. Int. Edit., Sep. 1, 2014, pp. 9430-9448, vol. 53, No. 36, Wiley-VCH Verlag GmbH & Co. KGaA, Weinheim.
EMD Millapore, "Crown ethers and Kryptofix for professional applications", accessed from: https://pr.vwr.com/assetsvc/asset/en_US/id/17030245/contents, Oct. 2015, pp. 1-4.
Fiel, S.A.,"Pre-concentration of Positron-emitting [18F]Fluoride and Radiosynthesis of Fluoride-based Prosthetic compounds for PET imaging using magnetic droplet microfluidics (MDM)", Simon Fraser University, 2014, pp. 1-100.

(Continued)

*Primary Examiner* — Michael G. Hartley
*Assistant Examiner* — Lance W Rider
(74) *Attorney, Agent, or Firm* — Armstrong Teasdale LLP

(57) ABSTRACT

Described herein are methods and devices that allow the generation of [F-18]triflyl fluoride and other [F-18] sulfonyl fluorides (such as [F-18]tosyl fluoride) in a manner that is suitable for radiosynthesis of F-18 labeled radiopharmaceuticals using currently available synthesis modules.

20 Claims, 5 Drawing Sheets

(56) References Cited

OTHER PUBLICATIONS

Fiel et al., "Magnetic Droplet Microfluidics as a Platform for the Concentration of [18F]Fluoride and Radiosynthesis of Sulfonyl [18F]Fluoride," ACS Appl. Mater. Interfaces, 2015, pp. 12923-12929, vol. 7, No. 23, American Chemical Society.

Gatley, S., "Rapid Production and Trapping of [18F]fluorotrimethylsilane, and its use in nucleophilic fluorine-18 labeling without an aqueous evaporation step," Intnl. J. Radiation Appl. Instrumentation. Part A. Appl. Radiat. Isotopes, 1989, pp. 541-544, vol. 40, No. 6, Elsevier Ltd.

He et al., "Advances in processes for PET radiotracer synthesis: Separation of [18F]fluoride from enriched [18O] water," Appl, Radiat. Isotopes, Sep. 2014, pp. 64-70, vol. 91, Elsevier Ltd.

Inkster et al., "Sulfonyl Fluoride-Based Prosthetic Compounds as Potential 18F Labelling Agents," Chem. Eur. J., Aug. 27, 2012, pp. 11079-11087, vol. 18, No. 35, Wiley-VCH Verlag.

Inkster et al., "Assessing the potential of sulfonyl fluorides as F-18-bearing prosthetic molecules," J. Labelled Compd. Radiopharma., 2011, p. S75, vol. 54, Wiley-Blackwell, Malden, MA.

Jiang et al., "Production and Transport of Gaseous 18F-Synthons: 18F-Acyl Fluorides," HHS Public Access Author Manuscript, available in PMC on Dec. 1, 2016, pp. 1-13, published in final edited form as: J. Fluor. Chem., Dec. 2015, pp. 181-185, vol. 180.

Lemaire et al., "Fast Production of Highly Reactive No-Carrier-Added [18F]Fluoride for the Labeling of Radiopharmaceuticals," Angew. Chem. Int. Edit., Apr. 19, 2010, pp. 3161-3164, vol. 49, No. 18, Wiley-VCH Verlag.

Lindner et al., "Azeotropic drying free [18F]FDG synthesis and its application to a lab-on-chip platform," Chem. Commun., 2016, pp. 729-732, vol. 52, The Royal Society of Chemistry.

Matesic et al., "Ascertaining the Suitability of Aryl Sulfonyl Fluorides for [18F]Radiochemistry Applications: A Systematic Investigation using Microfluidics," J. Org. Chem., 2013, pp. 11262-11270, vol. 78, American Chemical Society.

Matesic et al., "A systematic investigation into the F-18-radiolabelling and stability of sulfonyl fluorides using microfluidics," J. Labelled Compd. Radiopharma., 2013, p. S475, vol. 56, Wiley-Blackwell, Hoboken, NJ.

Mulholland, G., "Recovery and Purification of No-carrier-added [18F]Fluoride with Bistrimethylsilysulfate (BTMSS)," Appl. Radiat. !sot., 1991, pp. 1003-1008, vol. 42, No. 11, Pergamon Press plc.

Murakami et al., "Novel preconcentration technique using bis(2-ethylhexyl) hydrogen phosphate (HDEHP) loaded porous polytetrafluoroethylene (PTFE) filter tube as a sorbent: Its application to determination of In(III) in seawater by ICP-MS with air segmented", Anal. Chim. Acta, 2006, pp. 423-429.

Neal et al., "Improved synthesis of 18F-fluoromethyl tosylate, a convenient reagent for radiofluoromethylations", J Label Comp. and Radiopharm., 2005, pp. 557-568.

Nielsen et al., "A Low-Cost, Stable, and Selective Deoxyfluorination Reagent." J. Am. Chem. Soc., Jul. 15, 2015, pp. 9571-9574, vol. 137, American Chemical Society.

Ohsaki et al., "Polymer-supported catalysts for efficient on-column preparation of 2-deoxy-2-[18F]fluoro-D-glucose," Appl. Radiat. Isotopes, Apr. 1998, pp. 373-378, vol. 49, No. 4, Elsevier Science Ltd., Great Britain.

Pees et al., "Fast and reliable generation of [18F]triflyl fluoride a gaseous [18F]fluoride source", Chem. Commun., 2018, vol. 54, pp. 10179-10182.

Richarz et al., "Neither azeotropic drying, nor base nor other additives: a minimalist approach to 18F-labeling," Drg. Biomol. Chem., 2014, pp. 8094-8099, vol. 12, The Royal Society of Chemistry.

Seo et al., "Fast and Easy Drying Method for the Preparation of Activated [18F]Fluoride Using Polymer Cartridge," 2011, Korean Chem. Soc., 2011, pp. 71-76, vol. 32, No. 1.

Sewing et al. "A new nucleophilic radiofluorination reagent for fast and mild radiofluorination reaction," 21st International Symposium on Radiopharmaceutical Sciences, Oral Presentations, J. Label. Compd. Radiopharm., May 26-31, 2015, p. S2, vol. 58.

Tang et al., "Fully automated synthesis module for preparation of S-(2-[18F]fluoroethyl)-L-methionine by direct iucleophilic exchange on a quaternary 4-aminopyridinium resin," Nucl. Med. Biol., May 2003, pp. 509-512, vol. 30, No. 5, Elsevier Inc.

Toorongian et al., "Routine Production of 2-Deoxy-24189fluoro-D-Glucose by Direct Nucleophilic Exchange on a Quaternary 4-Aminopyridinium Resin," Nucl. Med. Biol., 1990, pp. 273-279, vol. 17, No. 3, Pergamon Press plc, Great Britain.

Wainerdi et al., "Modern Methods of Geochemical Analysis", Springer, 1971, pp. 89.

Wang et al., "Microfluidics for Positron Emission Tomography (PET) Imaging Probe Development", Mol Imaging, Aug. 2010, vol. 9, No. 4, pp. 175-191.

\* cited by examiner

METHODS AND DEVICES TO GENERATE [F-18]TRIFLYL FLUORIDE AND OTHER [F-18] SULFONYL FLUORIDES

CROSS-REFERENCE TO RELATED APPLICATIONS

This application claims priority to U.S. Provisional Application Ser. No. 62/961,521, filed on Jan. 15, 2020, and is a continuation-in-part of U.S. patent application Ser. No. 15/403,954, filed on Jan. 11, 2017, which claims priority to U.S. Provisional Application Ser. No. 62/277,222, filed on Jan. 11, 2016, the contents of which are hereby incorporated by reference in their entirety.

GOVERNMENT SUPPORT CLAUSE

This invention was made with government support under CA025836 awarded by the National Institutes of Health. The government has certain rights in the invention.

FIELD OF THE DISCLOSURE

Described herein are methods and devices that allow the generation of [F-18]triflyl fluoride and other [F-18] sulfonyl fluorides (such as [F-18]tosyl fluoride) in a manner that is suitable for radiosynthesis of F-18 labeled radiopharmaceuticals using currently available synthesis modules. The methods and devices described herein can simply generate [F-18]triflyl fluoride in short time and in high yield, and are compatible with currently available radiosynthesis modules.

BACKGROUND OF THE DISCLOSURE

[F-18]triflyl fluoride and other [F-18] sulfonyl fluorides (including [F-18]tosyl fluoride) have been demonstrated to provide a solution for current preparation of F-18 radiopharmaceuticals and for future needs of on-demand synthesis and personalized health care.

Conventionally, a syringe pump is commonly used in methods related to the generation of [F-18]triflyl fluoride and other [F-18] sulfonyl fluorides. However, syringe pumps present several difficulties for such applications. For example, previously reported methods to prepare [F-18] triflyl fluoride involve multiple steps (including trapping [F-18]fluoride in cartridge, eluting from the cartridge, reaction and removal from reaction mixture, drying by a drying column, and trapping [F-18]triflyl fluoride for labeling).

In contrast, for the preparation of [F-18]triflyl fluoride in the methods described herein, a separator (an empty cartridge, a vial with needles, or a cartridge with inert materials) is used to separate [F-18]triflyl fluoride from the reaction mixture using the air flow provided by the pump. No drying of [F-18]triflyl fluoride by drying agents as reported is needed for this process. For the preparation of [F-18]tosyl fluoride, circulating the eluting agent (tosyl chloride in acetonitrile) through the ionic exchange cartridge allows the preparation of [F-18]tosyl fluoride in high purity and in minimal volume that is suitable for radiosynthesis. This method can be integrated into a radiosynthesis module.

Described herein are methods and devices that allow the generation of [F-18]triflyl fluoride and other [F-18] sulfonyl fluorides (such as [F-18]tosyl fluoride) in manners that are suitable for radiosynthesis of F-18 labeled radiopharmaceuticals using currently available synthesis modules. A peristaltic pump is used to load [F-18]fluoride onto an ionic exchange cartridge, to load acetonitrile to rinse the cartridge in order to dry it, to load reagents to elute radioactivity, to circulate reaction mixture through a cartridge, and to provide air flow to separate [F-18]triflyl fluoride from the reaction mixture. This peristaltic pump design allows multiple jobs using the same pump.

The methods and devices described herein generate [F-18]triflyl fluoride in short time and in high yield, and are compatible with currently available radiosynthesis modules.

BRIEF DESCRIPTION OF THE DISCLOSURE

In one aspect, described herein is a method of making [F-18]sulfonyl fluoride without any evaporation step, wherein all method steps are performed with a single peristaltic pump. The method comprises passing an aqueous [F-18]fluoride solution or solvent through a solid phase extraction column comprising an anion-exchange resin so that the [F-18]fluoride is trapped on the resin, rinsing the resin with an organic solvent to eliminate residual water, and eluting the [F-18]fluoride with an eluting solution to release the [F-18]fluoride from the anion-exchange resin as [F-18] $RSO_2F$ which acts as a source of [F-18]fluoride for a labeling reaction. The eluting solution comprises a compound having the formula $RSO_2R^1$ and an organic solvent, wherein R is selected from the group consisting of hydrocarbyl, substituted hydrocarbyl, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heteroaryl, substituted heteroaryl, methyl, trifluoromethyl, and combinations thereof, and $R^1$ is a leaving group.

DETAILED DESCRIPTION OF THE DRAWINGS

The figures depict embodiments in accordance with the present disclosure and are not to be construed as limiting.

Figure 1:
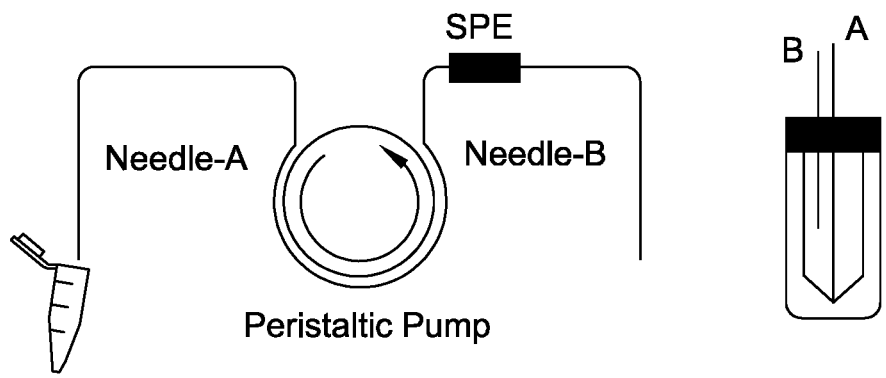
FIG. 1 depicts a schematic showing an exemplary embodiment for the preparation of [$^{18}$F]TsF using a peristaltic pump in accordance with the present disclosure.

The exemplary embodiment of FIG. 1 depicts an exemplary scheme for the preparation of [$^{18}$F]tosyl fluoride ([$^{18}$F]TsF) using a peristaltic pump.

Figure 2:
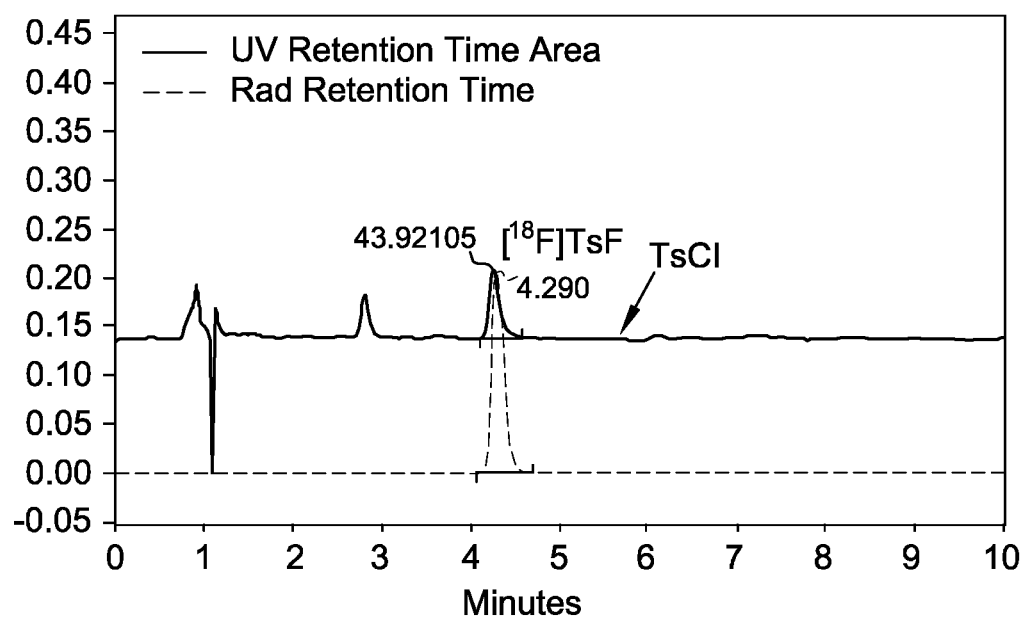
FIG. 2 depicts data for a Radio-HPLC of purified [$^{18}$F]TsF in accordance with the present disclosure.

The exemplary embodiment of FIG. 2 depicts a Radio-HPLC of purified [$^{18}$F]TsF. The black line shows the UV data and the dashed line shows the radioactivity data. The peaks at 4.3 minutes are [$^{18}$F]TsF. The peak of TsCl at 5 min is completely gone. [$^{18}$F]TsF (25.9 mCi) was generated in 96.7% radiochemical yield in acetonitrile (1 mL) with specific activity of 1645 mCi/μmol.

Figure 3:
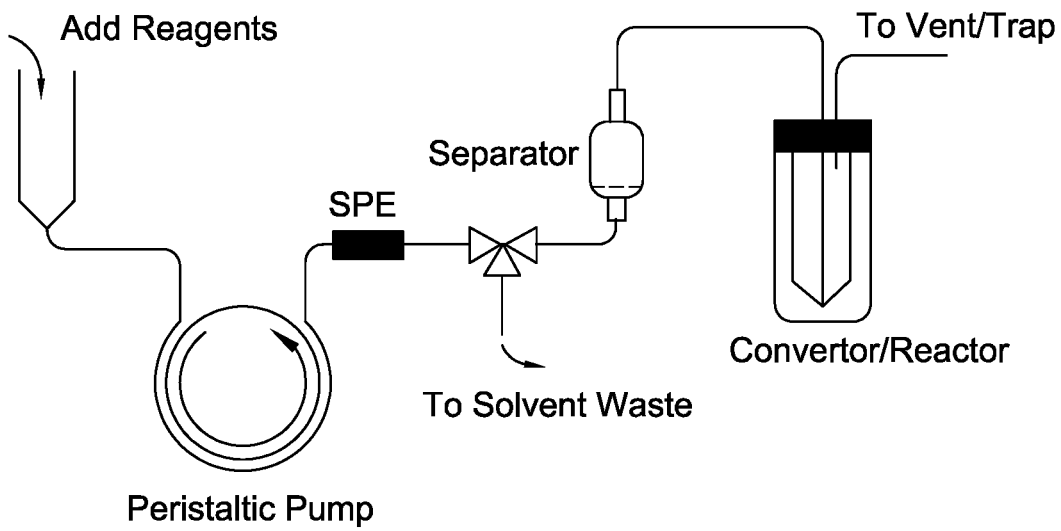
FIG. 3 depicts a schematic showing an exemplary embodiment for the preparation of [$^{18}$F]TfF using a peristaltic pump in accordance with the present disclosure.

The exemplary embodiment of FIG. 3 depicts an exemplary scheme for the preparation of [$^{18}$F]triflyl fluoride ([$^{18}$F]TfF) using a peristaltic pump.

Figure 4:
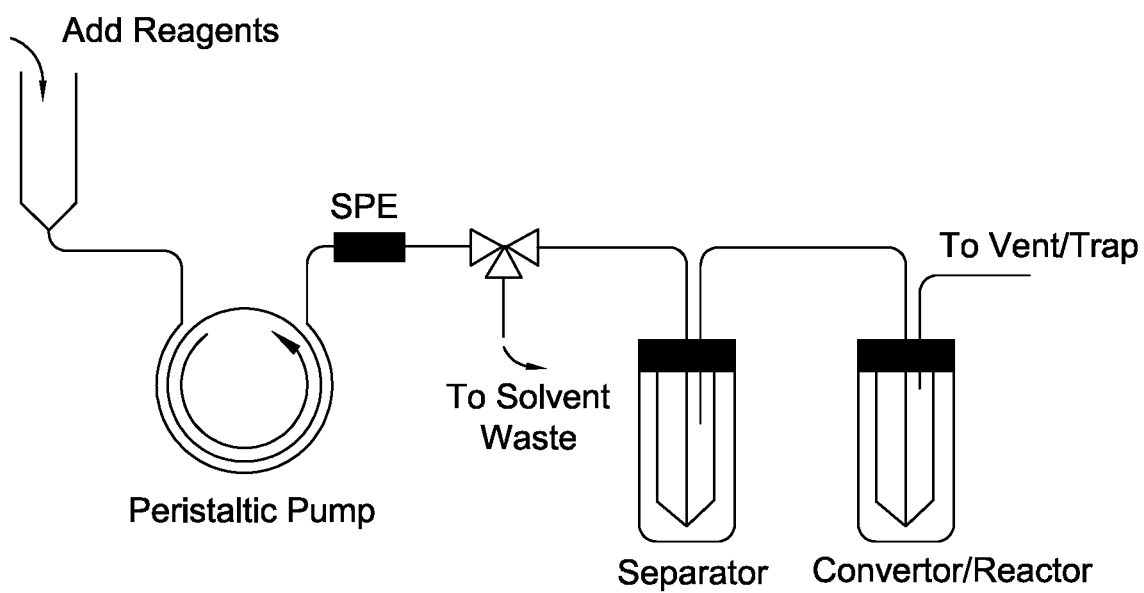
FIG. 4 depicts a schematic showing an exemplary embodiment for the preparation of [$^{18}$F]TfF using a peristaltic pump in accordance with the present disclosure.

The exemplary embodiment of FIG. 4 depicts an exemplary scheme for the preparation of [$^{18}$F]TfF using a peristaltic pump.

Figure 5:
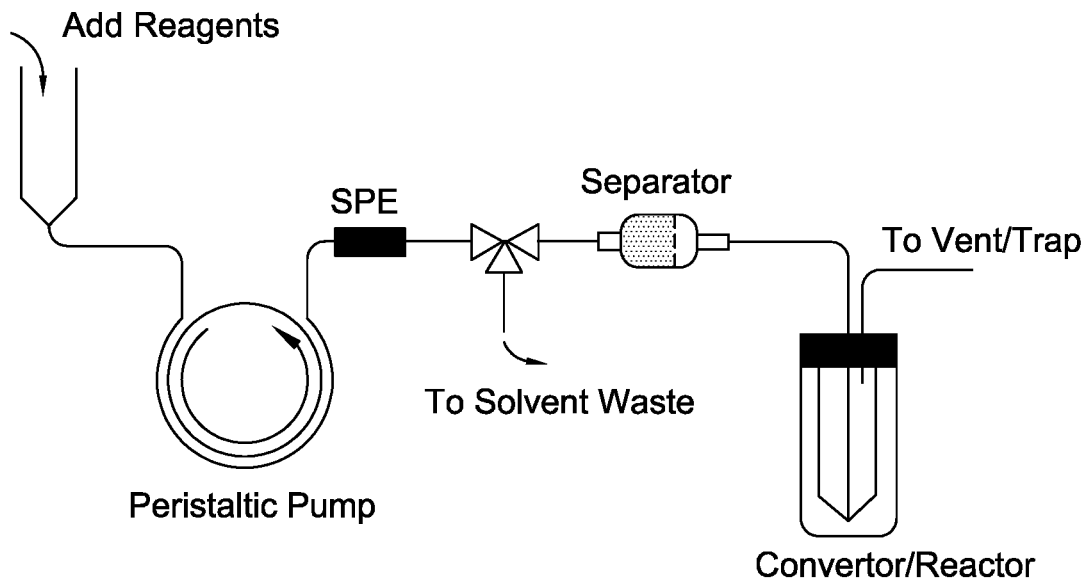
FIG. 5 depicts a schematic showing an exemplary embodiment for the preparation of [$^{18}$F]TfF using a peristaltic pump in accordance with the present disclosure.

The exemplary embodiment of FIG. 5 depicts an exemplary scheme for the preparation of [$^{18}$F]TfF using a peristaltic pump.

Figure 6:
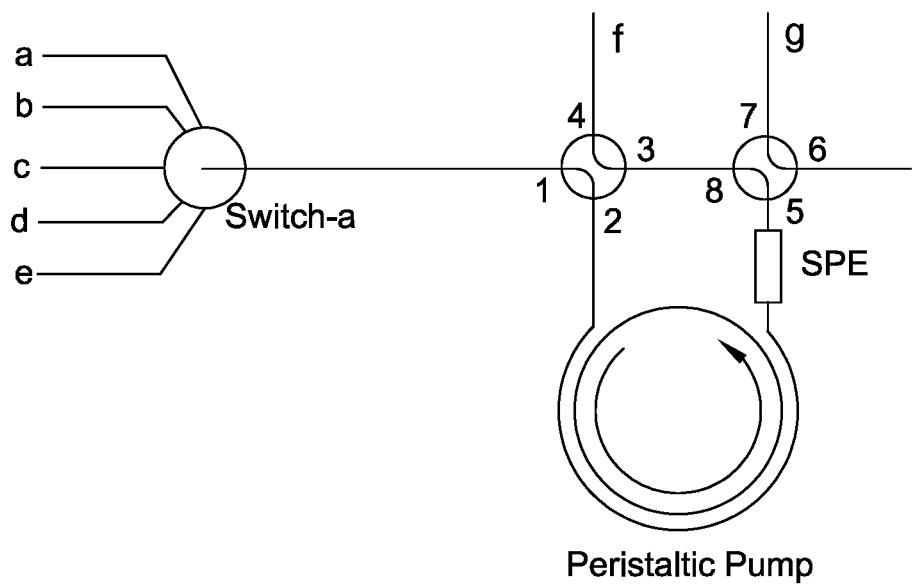
FIG. 6 depicts a schematic showing an exemplary embodiment for the design of a [$^{18}$F]TsF and [$^{18}$F]TfF generator in accordance with the present disclosure.

The exemplary embodiment of FIG. 6 depicts an exemplary scheme for the design of a [$^{18}$F]TsF and [$^{18}$F]TfF generator. Switch-a is connected to different ports (ports a, b, c, d, and e) for loading [$^{18}$F]fluoride, reagents, solvents, air or inert gas, etc. Four-way switches f and g are set up for the elution. Switch-f has four ports: ports 1, 2, 3, and 4. Switch-g has four ports: ports 5, 6, 7, and 8. Each switch can be rotated to alter the flow path. For example, once [$^{18}$F] fluoride is trapped and dried in the solid phase extraction (SPE) column, elution agents are loaded into the pump and SPE column. Ports 2 and 3 of switch-f and ports 5 and 8 of switch-g are on for circulation. When the circulation is completed, port 1 and 2 are on and [$^{18}$F]TsF can be eluted through port 4. There are many options for this setup that are not limited to the embodiments described herein.

Figure 7A:
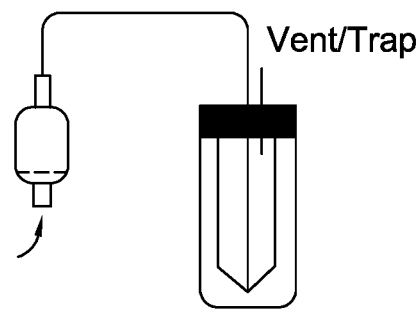
FIG. 7A depicts a schematic showing an exemplary embodiment for the separation of [$^{18}$F]TfF from eluted solution in accordance with the present disclosure.
Figure 7B:
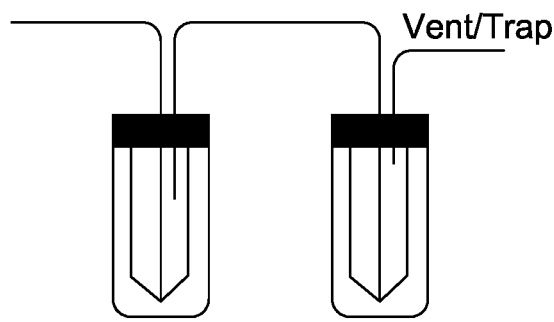
FIG. 7B depicts a schematic showing an exemplary embodiment for the separation of [$^{18}$F]TfF from eluted solution in accordance with the present disclosure.
Figure 7C:
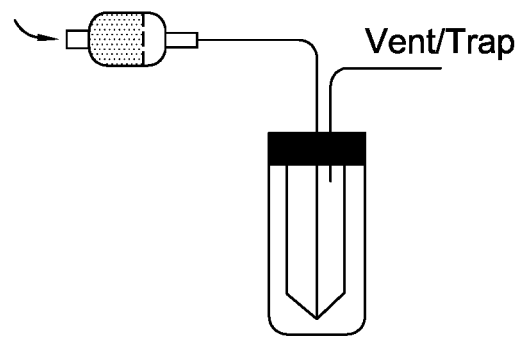
FIG. 7C depicts a schematic showing an exemplary embodiment for the separation of [$^{18}$F]TfF from eluted solution in accordance with the present disclosure.
Figure 7D:
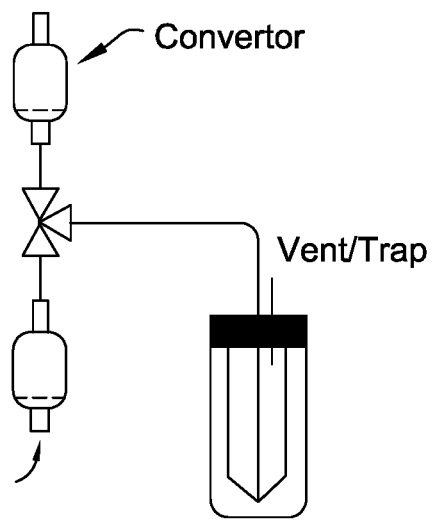
FIG. 7D depicts a schematic showing an exemplary embodiment for the separation of [$^{18}$F]TfF from eluted solution in accordance with the present disclosure.

The exemplary embodiment of FIGS. 7A-7D depict exemplary schemes for the separation of [$^{18}$F]TfF from eluted solution. FIG. 7A depicts separation via an empty cartridge (with or without a frit or frits). Frits are filters that are commonly used in commercially available SPE columns and cartridges to provide support for resins and even flow through resins. They are made of Polyethylene (PE), Polypropylene (PP), PTFE or other materials. FIG. 7B depicts separation via bubbling in a V vial. FIG. 7C depicts separation through an inert materials cartridge. FIG. 7D depicts separation through conversion in a secondary empty cartridge and transference to a reaction vial.

Figure 8:
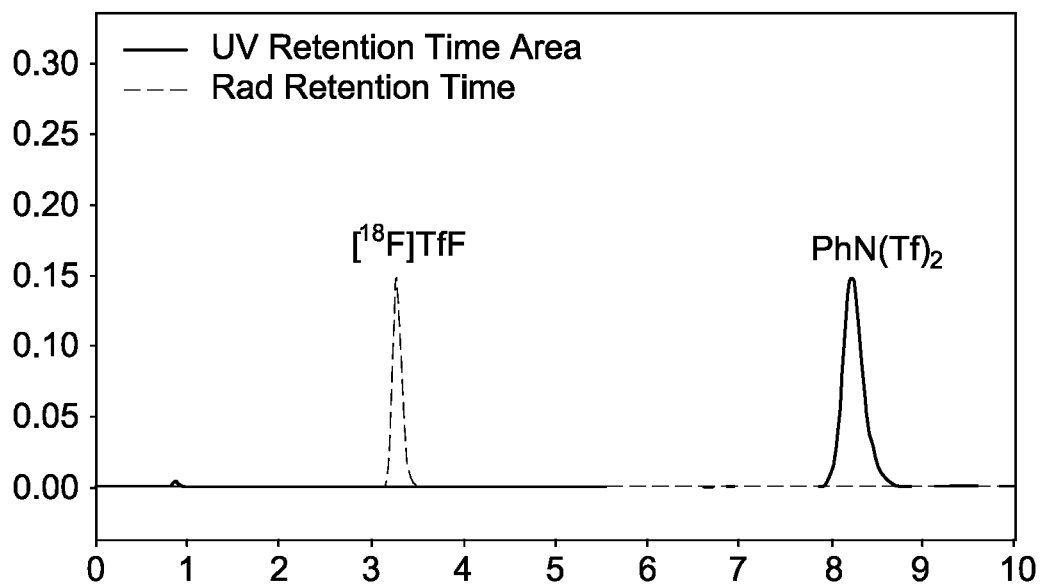
FIG. 8 depicts data for a Radio-HPLC of [$^{18}$F]TfF after eluting from cartridge using PhN(Tf)$_2$ in accordance with the present disclosure.

The exemplary embodiment of FIG. 8 depicts a Radio-HPLC of [$^{18}$F]TfF after eluting from cartridge using PhN(Tf)$_2$ without the separation step The solid line shows the UV data and the dashed line shows the radioactivity data. The peak of [$^{18}$F]TfF was observed at 3.3 min. However, significant amount of precursor PhN(Tf)$_2$ was observed at 8.3 min. [$^{18}$F]TfF with PhN(Tf)$_2$ is practically useless for radiolabeling. [$^{18}$F]TfF can be purified easily as described in the method by the separator, which separate [F-18]TfF from the eluted reaction mixture.

DETAILED DESCRIPTION OF THE DISCLOSURE

Described herein, the synthesis of [F-18] sulfonyl fluorides has been enhanced by using a single peristaltic pump.

In some aspects, eluting is done via a circulating method with the single peristaltic pump. In some aspects, the single peristaltic pump provides air flow to separate [F-18]sulfonyl fluoride from the reaction mixture.

As described herein, a separator is a device used to separate gaseous [$^{18}$F]TfF from non- or low-volatile solvents/reagents. As shown in FIG. 6, a commercially available empty solid phase extraction (SPE) cartridge allows such a separation. Bubbling air or other inert gas through the eluted solution also allows [$^{18}$F]TfF to be separated from the solution. A cartridge with material inert towards [$^{18}$F]TsF allows gas to pass while retaining eluted solution with the inert materials.

In some embodiments, a method of making [F-18]sulfonyl fluoride without any evaporation step is disclosed. The method comprises: a) passing an aqueous [F-18]fluoride solution or solvent through a solid phase extraction column comprising an anion-exchange resin so that the [F-18] fluoride is trapped on the resin; b) rinsing the resin with an organic solvent to eliminate the residual water; and c) eluting the [F-18]fluoride with an eluting solution to release the [F-18]fluoride from the anion-exchange resin as [F-18] RSO$_2$F which acts as a source of [F-18]fluoride for a labeling reaction, wherein the eluting solution comprises a compound having the formula RSO$_2$R$^1$ and an organic solvent, wherein R is selected from the group consisting of hydrocarbyl, substituted hydrocarbyl, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heteroaryl, substituted heteroaryl, methyl, trifluoromethyl, and combinations thereof;

R$^1$ is a leaving group; and wherein all method steps are performed with a single peristaltic pump.

In some embodiments of the present disclosure, the eluting is done via a circulating method with the single peristaltic pump.

In some embodiments, the single peristaltic pump provides air flow to separate [F-18]sulfonyl fluoride from the reaction mixture. In some embodiments, a separator is used to separate [F-18]triflyl fluoride from the reaction mixture using the air flow provided by the pump. In some embodiments, the separator is selected from the group consisting of an empty cartridge, a vial with needles, and a cartridge with inert materials.

In some embodiments, R is selected from the group consisting of alkyl, substituted alkyl, cycloalkyl, substituted cycloalkyl, aryl, substituted aryl, heteroaryl, substituted heteroaryl, methyl, and trifluoromethyl.

In some embodiments, R is selected from the group consisting of CH$_3$, CF$_3$, C$_6$H$_5$, CH$_3$C$_6$H$_4$, CF$_3$C$_6$H$_4$, NO$_2$C$_6$H$_4$, ClC$_6$H$_4$, FC$_6$H$_4$, BrC$_6$H$_4$, IC$_6$H$_4$, CH$_3$COC$_6$H$_4$, MeOC$_6$H$_4$, CNC$_6$H$_4$, Me$_2$NC$_6$H$_4$, 2,4,6-(CH$_3$)$_3$C$_6$H$_2$, and C$_5$H$_5$N (pyridine).

In some embodiments, R$^1$ is selected from the group consisting of Cl$^-$, Br$^-$, I$^-$, tosylate (TsO), mesylate (MsO), and trifluoromethanesulfate (triflate; TfO).

In some embodiments, RSO$_2$ is selected from the group consisting of tosyl (Ts), mesyl (Ms), trifluoromethanesulfonyl (Tf), nosyl (Ns), besyl (Bs), and N-phenyl-trifluoromethanesulfonimide (NTfPh).

In some embodiments, RSO$_2$R$^1$ is selected from the group consisting of tosyl chloride, mesyl chloride, trifluoromethanesulfonyl chloride, nosyl chloride, N-Phenyl-bis(trifluoromethanesulfonimide), tosyl anhydride, mesyl anhydride, trifluoromethanesulfonic anhydride, tosyl mesylate, and tosyl triflate.

In some embodiments, the organic solvent is selected from the group consisting of acetonitrile, dimethylformamide, 2-amyl alcohol, tetrahydrofuran, and ethanol.

In some embodiments, the eluting solution further comprises a co-eluting agent selected from the group consisting of TsOH/TsO$^-$, MsOH/MsO$^-$, TfOH/TfO$^-$, HCl/O$^-$, $H_2SO_4$/$HSO_4^-$/$SO_4^{2-}$, AcOH/AcO$^-$ and TsOH·$H_2O$.

In some embodiments, the anion exchange resin comprises a polymeric matrix and quaternary ammonium groups.

In some embodiments, the method further comprises regenerating the [F-18]fluoride in the presence of at least one base and at least one phase transfer catalyst during or before a labeling reaction.

In some embodiments, the base is selected from the group consisting of potassium carbonate ($K_2CO_3$), potassium bicarbonate ($KHCO_3$), cesium carbonate ($Cs_2CO_3$), cesium biocarbonate, and tetrabutylammonium and tetramethylammonium salts (hydroxide, carbonate, and bicarbonate).

In some embodiments, the base and phase transfer catalyst are selected from the group consisting of potassium carbonate/Kryptofix 222, potassium bicarbonate/Kryptofix 222, potassium carbonate/18-crown-6, and potassium bicarbonate/18-crown-6.

In some embodiments, the base and phase transfer catalyst are pre-dried prior to use.

In some embodiments, regeneration is carried out under anhydrous or aqueous conditions.

In some embodiments, the [F-18]sulfonyl fluoride is used to measure concentration and specific activity of fluoride.

In some embodiments, the eluted solution containing the [F-18]sulfonyl fluoride is used for the synthesis of a PET radiotracer.

EXAMPLES

Example 1. Preparation of [$^{18}$F]TsF Using a Peristaltic Pump

Experimental Conditions
Pump: Cole-Parmer Masterflex L/S (07557-14)
Pump Head: Masterflex L/S Standard Pump Head for L/S 14
Tubing, PPS Housing/SS Rotor (EW-07014-52)
Tubing: Masterflex C-Flex ULTRA tubing, L/S 14 (06434-14)
Flow rate: 3 mL/min
Void volume (from needle-A to needle-B): <0.5 mL
Procedure This Example was prepared according to the scheme of FIG. 1.

[$^{18}$F]fluoride (1-50 mCi) in [$^{18}$O]water (0.1-0.5 mL in a syringe) from a cyclotron was transferred to a vial. The residual radioactivity in the syringe was rinsed with MQ water (1 mL), and all radioactivity was combined in the vial. The radioactivity was loaded through needle-A and trapped in the SPE (Chromafix 30PS-HCO3 cartridge or Bio-Rad AG MP-1M-HCO$_3$ 30 mg, made in-house) in about 0.5 min via the peristaltic pump. MQ water (1 mL), followed by acetonitrile (1 mL), was added to the vial to rinse the system. Acetonitrile (5 mL) in another vial was used to dry the cartridge. A solution of TsCl (1 mg) and TsOH·$H_2O$ (0.25 mg) in acetonitrile (0.5 mL) in the V vial (as shown in FIG. 1) was circulated for 3 min at room temperature. The following two steps present two separate procedural options. These options are not limiting.

In option 1, the solution was delivered to a reaction vial from needle-B, and followed by the system being rinsed with acetonitrile (0.5 mL). Up to 98% radioactivity was transferred to the reaction vial and 2% radioactivity was left in the SPE column (30P5-HCO$_3$).

In option 2, the system was rinsed with acetonitrile (0.5 mL) from needle-A, and all radioactivity was collected in the vial as shown above. The collected radioactivity can be distributed for several reactions.

Results

Radio-HPLC data of purified [$^{18}$F]TsF prepared according to this example, utilizing option 1, are shown in FIG. 2. [$^{18}$F]TsF (25.9 mCi) was generated in 96.7% radiochemical yield in acetonitrile (1 mL) with specific activity of 1645 mCi/µmol.

Example 2. Preparation of [$^{18}$F]TfF Using a Peristaltic Pump

This Example was prepared according to the scheme of FIG. 3.

Experimental Conditions
Pump: Cole-Parmer Masterflex L/S (07557-14)
Pump Head: Masterflex L/S Standard Pump Head for L/S 14
Tubing, PPS Housing/SS Rotor (EW-07014-52)
Tubing: Masterflex C-Flex ULTRA tubing, L/S 14 (06434-14)
Flow rate: 3 mL/min or 10 mL/min
Void volume (from needle-A to needle-B): <0.5 mL
Procedure

[$^{18}$F]fluoride in [$^{18}$O]water (0.1-0.5 mL in a syringe) from a cyclotron was transferred to a vial. The residual radioactivity in the syringe was rinsed with MQ water (1 mL), and all radioactivity was combined in the vial. The radioactivity was then added to the reservoir (see FIG. 3) and loaded onto the SPE (Chromafix 30PS-HCO$_3$ cartridge or Bio-Rad AG MP-1M-HCO$_3$ 30 mg, made in-house) via the peristaltic pump at 10 mL/min. Eluted solvent was directed to the solvent waste container. MQ water (1 mL) was added to rinse the system at 10 mL/min. Acetonitrile (3 mL) was added to dry the cartridge at 10 mL/min. A solution of N-Phenyl-bis(trifluoromethanesulfonimide) (Tf$_2$NPh) (5-10 mg) in acetonitrile (0.1-0.5 mL) was added and eluted to the separator at 3 mL/min at room temperature for 5 min. [$^{18}$F]TfF was trapped in the convertor/reactor, which contained $K_2CO_3$/$K_{222}$ in acetonitrile.

Results

Radio-HPLC Data of [$^{18}$F]TfF after eluting from the cartridge using PhN(Tf)$_2$ are shown in FIG. 8. The solid line shows the UV data and the dashedline shows the radioactivity data. The peak of [$^{18}$F]TfF was observed at 3.3 min. However, significant amount of precursor PhN(Tf)$_2$ was observed at 8.3 min. [$^{18}$F]TfF with PhN(Tf)$_2$ is practically useless for radiolabeling. [$^{18}$F]TfF can be purified easily as described in the method by the separator, which separate [F-18]TfF from the eluted reaction mixture.

Example 3. Synthesis of [$^{18}$F]Fludeoxyglucose (FDG) Intermediate

Experimental Conditions
Reagent: Tf$_2$NPh (10 mg) in acetonitrile (0.3 mL)
SPE: Bio-Rad AG MP-1M-HCO$_3$ (30 mg)
Separator: Supelco® 1 mL empty polypropylene SPE Tube with PE fits Trapping agent in convertor: $K_2CO_3/K_{222}$ (1.6 mg) in acetonitrile (0.5 mL)

Procedure

This Example was prepared according to the scheme of FIG. 3.

[$^{18}$F]fluoride (~4 mCi) in water (1 mL) was added to the reservoir (see FIG. 3) and loaded onto the SPE (Bio-Rad AG MP-1M-HCO3 30 mg, made in-house) via the peristaltic pump at 10 mL/min. Eluted solvent was directed to the solvent waste container. MQ water (1 mL) was added to rinse the system at 10 mL/min. Acetonitrile (3 mL) was added to dry the cartridge at 10 mL/min. A solution of N-Phenyl-bis(trifluoromethanesulfonimide) (Tf$_2$NPh) (10 mg) in acetonitrile (0.3 mL) was added and eluted into a 1 mL empty SPE tube with PE fit on the bottom at 3 mL/min at room temperature for 5 min. [$^{18}$F]TfF was trapped in the convertor/reactor, which contained $K_2CO_3/K_{222}$ (1.6 mg) in acetonitrile (0.5 mL).

Results

Radioactivity left in SPE: 0.136 mCi (3.2%)
Radioactivity left in separator: 0.03 mCi (1%)
Radioactivity left trapped: 3.87 mCi (91.3%)
Radioactivity left in vent trap (alumina-N 1000 mg): 0.20 mCi (4.7%)
Radiosynthesis of FDG:
The above radioactivity was added to FDG precursor (4.8 mg), and then heated at 75° C. for 10 min.
RadioTLC indicated 93% radiochemical conversion as the FDG intermediate.

Example 4. Synthesis of [$^{18}$F]FluorThanatrace ([$^{18}$F]FTT)

Experimental Conditions
[$^{18}$F]fluoride: 43 mCi in 0-18 water
Reagent: Tf$_2$NPh (10 mg) in acetonitrile (0.3 mL)
SPE: Bio-Rad AG MP-1M-HCO$_3$ (30 mg)
Separator: Supelco® 1 mL empty polypropylene SPE Tube with PE fits
Trapping agent in convertor: $K_2CO_3/K_{222}$ (2.5 mg) and FTT precursor (1.1 mg) in acetonitrile (0.5 mL)
Procedure This Example was prepared according to the scheme of FIG. 3.

[$^{18}$F]fluoride (43.1 mCi) in water (0.6 mL) was added to the reservoir (see FIG. 3) and loaded onto the SPE (Bio-Rad AG MP-1M-HCO3 30 mg, made in-house) via the peristaltic pump at 10 mL/min. Eluted solvent was directed to the solvent waste container. MQ water (1 mL) was added to rinse the system at 10 mL/min. Acetonitrile (5 mL) was added to dry the cartridge at 10 mL/min. A solution of N-Phenyl-bis(trifluoromethanesulfonimide) (Tf$_2$NPh) (10 mg) in acetonitrile (0.3 mL) was added and eluted into a 1 mL empty SPE tube with PE frit on the bottom at 3 mL/min at room temperature for 5 min. [$^{18}$F]TfF was trapped in the convertor/reactor, which contained $K_2CO_3/K_{222}$ (2.5 mg) and FTT tosylate precursor (1.1 mg) in acetonitrile (0.5 mL).

Results

Radioactivity left in SPE: 1.4 mCi (3.8%)
Radioactivity left in separator: 2.06 mCi (5.5%)
Radioactivity left trapped: 33.2 mCi (89%)
Radioactivity left in vent trap (alumina-N 1000 mg): 0.14 mCi (0.38%)
The above reaction mixture was heated at 108° C. for 10 min, and then diluted with 0.1% trifluoroacetic acid in water (4 mL) for HPLC purification to afford 15 mCi final product (57% decay corrected yield) with specific activity of 1180 mCi/μmol at the end of synthesis.

Example 5. Synthesis of [$^{18}$F]FDMT/(6-[4-[[1-(2-[$^{18}$F]fluoroethyl)-1H-1,2,3-triazol-4-yl]methoxy]phenyl]-5,6-dihydro-5-methyl-3,8-Phenanthridinediamine) (as Boc-Protected Intermediate)

Experimental Conditions
Reagent: Tf$_2$NPh (10 mg) in acetonitrile (0.1 mL), 10 mL/min
SPE: Bio-Rad AG MP-1M-HCO$_3$ (30 mg)
Separator: V-shape vial (1 mL)
Trapping agent in convertor: $K_2CO_3/K_{222}$ (2.5 mg) in acetonitrile (0.5 mL)
Procedure This Example was prepared according to the scheme of FIG. 4.

[$^{18}$F]fluoride in water (0.5 mL) was added to the reservoir (see FIG. 4) and loaded onto the SPE (Bio-Rad AG MP-1M-HCO3 30 mg, made in-house) via the peristaltic pump at 10 mL/min. Eluted solvent was directed to the solvent waste container. MQ water (1 mL) was added to rinse the system at 10 mL/min. Acetonitrile (5 mL) was added to dry the cartridge at 10 mL/min. A solution of N-Phenyl-bis(trifluoromethanesulfonimide) (Tf$_2$NPh) (10 mg) in acetonitrile (0.1 mL) was added and eluted into a V-shape vial (1 mL) via a needle (which was inserted to the bottom of the vial) at 3 mL/min at room temperature for 5 min. [$^{18}$F]TfF was trapped in the convertor/reactor, which contained $K_2CO_3/K_{222}$ (2.5 mg) in acetonitrile (0.5 mL).

Results

Radioactivity left in SPE: 0.10 mCi (3.5%)
Radioactivity left in separator: 0.03 mCi (1%)
Radioactivity left trapped: 2.65 mCi (91.6%)
Radioactivity left in vent trap (alumina-N 1000 mg): 0.11 mCi (3.8%)

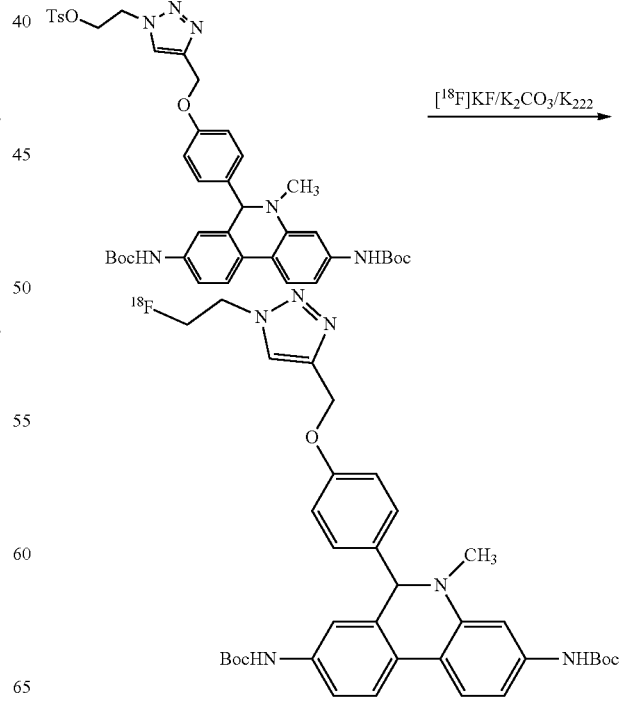

The above radioactivity was added to FDMT-OTs precursor (2.4 mg), and then heated at 86° C. for 10 min. RadioTLC of reaction solution indicated 83% radiochemical conversion, which was confirmed by radio-HPLC. 7.4% of total radioactivity is insoluble.

Example 6. Carrier-Added Synthesis of [$^{18}$F]TfF

Experimental Conditions
Reagent: KF (0.1 μmol) as carrier to simulate mass from 1000 mCi fluoride with specific activity of 10000 mCi/μmol.
Tf$_2$NPh (10 mg) in acetonitrile (0.1 mL), 10 mL/min
SPE: Bio-Rad AG MP-1M-HCO$_3$ (30 mg)
Separator: V-shape vial (1 mL)
Trapping agent in convertor: K$_2$CO$_3$/K$_{222}$ (50 mg) in acetonitrile (0.5 mL)
Procedure
This Example was prepared according to the scheme of FIG. 4.
[$^{18}$F]fluoride (~3 mCi) and potassium fluoride (0.1 μmol) in water (0.5 mL) was added to the reservoir (see FIG. 4) and loaded onto the SPE (Bio-Rad AG MP-1M-HCO3 30 mg, made in-house) via the peristaltic pump at 10 mL/min. Eluted solvent was directed to the solvent waste container. MQ water (1 mL) was added to rinse the system at 10 mL/min. Acetonitrile (5 mL) was added to dry the cartridge at 10 mL/min. A solution of N-Phenyl-bis(trifluoromethanesulfonimide) (Tf$_2$NPh) (10 mg) in acetonitrile (0.1 mL) was added and eluted into a V-shape vial (1 mL) via a needle (which was inserted to the bottom of the vial) at 3 mL/min at room temperature for 5 min. [$^{18}$F]TfF was trapped in the convertor/reactor, which contained K$_2$CO$_3$/K$_{222}$ (50 mg) in acetonitrile (0.5 mL).
Results
Radioactivity left in SPE: 0.039 mCi (1%)
Radioactivity left in separator: 0.04 mCi (1%)
Radioactivity left trapped: 3.55 mCi (98%)
Radioactivity left in vent trap (alumina-N 1000 mg): 0.004 mCi (0%)

Example 7. Synthesis of methyl 4-[$^{18}$F]fluoro-1-naphthoate Using [$^{18}$F]TfF Experimental Conditions
Tf$_2$NPh (10 mg) in acetonitrile (0.1 mL), flow rate: 10 mL/min.
SPE: Bio-Rad AG MP-1M-HCO$_3$ (30 mg)
Separator: V-shape vial (1 mL)
Trapping agent in convertor: K$_2$CO$_3$/K$_{222}$ (5 mg) and labeling precursor (4 mg) in acetonitrile (0.5 mL)

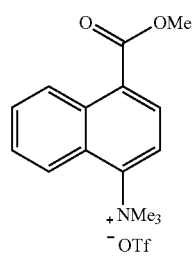

Procedure
This Example was prepared according to the scheme of FIG. 4.
[$^{18}$F]fluoride in water (0.5 mL) was added to the reservoir (see FIG. 4) and loaded onto the SPE (Bio-Rad AG MP-1M-HCO3 30 mg, made in-house) via the peristaltic pump at 10 mL/min. Eluted solvent was directed to the solvent waste container. MQ water (1 mL) was added to rinse the system at 10 mL/min. Acetonitrile (5 mL) was added to dry the cartridge at 10 mL/min. A solution of N-Phenyl-bis(trifluoromethanesulfonimide) (Tf$_2$NPh) (10 mg) in acetonitrile (0.1 mL) was added and eluted into a V-shape vial (1 mL) via a needle (which was inserted to the bottom of the vial) at 3 mL/min at room temperature for 5 min. [$^{18}$F]TfF was trapped in the convertor/reactor, which contained K$_2$CO$_3$/K$_{222}$ (5 mg) and 4-(methoxycarbonyl)-N,N,N-trimethylnaphthalen-1-aminium trifluoromethanesulfonate (4 mg) in acetonitrile (0.5 mL).
Results
Radioactivity left in SPE: 0.12 mCi (2.6%)
Radioactivity left in separator: 0.08 mCi (1.7%)
Radioactivity left trapped: 4.41 mCi (94%)
Radioactivity left in vent trap (alumina-N 1000 mg): 0.07 mCi (1.7%)
Radiosynthesis: The reaction mixture after trapping was heated at 110° C. for 10 min. RadioTLC indicated 95% radiochemical conversion, which was confirmed by Radio-HPLC.

Example 8. Synthesis of [$^{18}$F]FDG Intermediate

Experimental Conditions
Reagent: Tf$_2$NPh (10 mg) in acetonitrile (0.2 mL), flow rate=3 mL/min
SPE: Bio-Rad AG MP-1M-HCO$_3$ (30 mg)
Separator: Whatman® drying cartridge (Na$_2$SO$_4$/1.5 gram)
Trapping agent in convertor: K$_2$CO$_3$/K$_{222}$ (5 mg) in acetonitrile (0.5 mL)
Procedure
This Example was prepared according to the scheme of FIG. 5.
[$^{18}$F]fluoride in water (0.5 mL) was added to the reservoir (see FIG. 5) and loaded onto the SPE (Bio-Rad AG 1M-1M-HCO3 30 mg, made in-house) via the peristaltic pump at 10 mL/min. Eluted solvent was directed to the solvent waste container. MQ water (1 mL) was added to rinse the system at 10 mL/min. Acetonitrile (3 mL) was added to dry the cartridge at 10 mL/min. A solution of N-Phenyl-bis(trifluoromethanesulfonimide) (Tf2NPh) (10 mg) in acetonitrile (0.2 mL) was added and eluted through a Whatman® drying cartridge (containing 1.5 gram Na$_2$SO$_4$) at 3 mL/min at room temperature for 5 min. [$^{18}$F]TfF was trapped in the convertor/reactor, which contained K$_2$CO$_3$/K$_{222}$ (5 mg) in acetonitrile (0.5 mL).
Results
Radioactivity left in SPE: 0.062 mCi (4.1%)
Radioactivity left in separator: 0.04 mCi (2.7%)
Radioactivity left trapped: 1.28 mCi (85.1%)
Radioactivity left in vent trap (alumina-N 1000 mg): 0.122 mCi (8.1%)
The above radioactivity was added to FDG precursor (5 mg), and then heated at 60° C. for 9 min.
RadioTLC of reaction solution indicated 97% radiochemical conversion, which was confirmed by radio-HPLC. 3.9% of total radioactivity is insoluble.

Example 9. Synthesis of methyl 4-[$^{18}$F]fluoro-1-naphthoate Using [$^{18}$F]TfF Experimental Conditions
Reagent: Tf$_2$NPh (10 mg) in acetonitrile (0.2 mL), flow rate=3 mL/min
SPE: Bio-Rad AG MP-1M-HCO$_3$ (30 mg)
Separator: Whatman® drying cartridge (Na$_2$SO$_4$/1.5 gram)
Trapping agent in convertor: KHCO$_3$/K$_{222}$ (1 mg/3.75 mg) in acetonitrile (0.5 mL)

Procedure

This Example was prepared according to the scheme of FIG. 5.

[$^{18}$F]fluoride in water (0.5 mL) was added to the reservoir (see FIG. 5) and loaded onto the SPE (Bio-Rad AG MP-1M-HCO3 30 mg, made in-house) via the peristaltic pump at 10 mL/min. Eluted solvent was directed to the solvent waste container. MQ water (1 mL) was added to rinse the system at 10 mL/min. Acetonitrile (3 mL) was added to dry the cartridge at 10 mL/min. A solution of N-Phenyl-bis(trifluoromethanesulfonimide) (Tf$_2$NPh) (10 mg) in acetonitrile (0.2 mL) was added and eluted through a Whatman® drying cartridge (containing 1.5 gram Na$_2$SO$_4$) at 3 mL/min at room temperature for 5 min. [$^{18}$F]TfF was trapped in the convertor/reactor, which contained KHCO$_3$/K$_{222}$ (1 mg/3.75 mg) in acetonitrile (0.5 mL).

Results
Radioactivity left in SPE: 0.076 mCi (5.6%)
Radioactivity left in separator: 0.043 mCi (3.1%)
Radioactivity left trapped: 1.23 mCi (90%)
Radioactivity left in vent trap (alumina-N 1000 mg): 0.018 mCi (1.3%)

Radiosynthesis of methyl 4-[$^{18}$F]fluoro-1-naphthoate

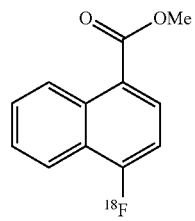 [SMILES: COC(=O)c1ccc([18F])c2ccccc12]

The above radioactivity was added to the precursor 4-(methoxycarbonyl)-N,N,N-trimethylnaphthalen-1-aminium trifluoromethanesulfonate (4 mg), and heated at 110° C. for 10 min. RadioTLC of reaction solution indicated 96% radiochemical conversion, which was confirmed by radio-HPLC. 3% of total radioactivity is insoluble.

Table 1 describes the eluting efficiency using common organic solvents acetonitrile (MeCN), DMSO, t-amyl alcohol and THF, which are also commonly used for $^{18}$F radiolabeling reactions.

TABLE 1

Eluting efficiency for a variety of eluting solvents (5 mg eluting agent Tf$_2$NPh at 3 mL/min, distilled at 10 mL/min, and trapped in K$_2$CO$_3$/K$_{222}$ (5 mg) in acetonitrile (0.5 mL)).

| Entry | Solvent (mL) | EE$^a$ (%) |
|---|---|---|
| 1 | MeCN (0.5 mL) | 96 |
| 2 | DMSO (0.5 mL) | 68 |
| 3 | t-amyl alcohol (0.5 mL) | 94 |
| 4 | THF (0.5 mL) | 95 |

$^a$EE/eluting efficiency (%) = radioactivity eluted/total of radioactivity.

Table 2 describes the trapping efficiency in the solution of K$_2$CO$_3$/K$_{222}$ and KHCO$_3$/K$_{222}$ and radiochemical yield of reaction-ready fluoride after the process (trapped radioactivity/total starting radioactivity). K$_2$CO$_3$/K$_{222}$ and KHCO$_3$/K$_{222}$ are commonly used bases for $^{18}$F radiolabeling. Cold fluoride was used to simulate an elution/trapping process in large amount of radioactivity.

TABLE 2

Trapping and isolated efficiencies (10 mg eluting agent Tf$_2$NPh in acetonitrile at 3 mL/min and distilled at 3 mL/min).

| Entry | Trapping agent (mg) | TE$^a$ (%) | RCY$^b$ (%) | Note$^c$ | Replicates |
|---|---|---|---|---|---|
| 1 | K$_2$CO$_3$/K$_{222}$ (5 mg) | 97.3 ± 1.1 | 92.4 ± 1.4 | | 3 |
| 2 | K$_2$CO$_3$/K$_{222}$ (5 mg) | 98.1 | 96.5 | 0.1 µmol fluoride added | 1 |
| 3 | K$_2$CO$_3$/K$_{222}$ (5 mg) | 91.4 | 86 | Trapped in 1:4 MeCN/Amyl alcohol (500 µL) | 1 |
| 4 | K$_2$CO$_3$/K$_{222}$ (2.5 mg) | 97.3 ± 1.5 | 90.5 ± 1.1 | | 3 |
| 5 | K$_2$CO$_3$/K$_{222}$ (2.5 mg) | 31.9 | 29.3 | Trapped in amyl alcohol (300 µL) | 1 |
| 6 | K$_2$CO$_3$/K$_{222}$ (2.5 mg) | 15.3 | 15.2 | 1 µmol fluoride added | 1 |
| 7 | K$_2$CO$_3$/K$_{222}$ (1 mg) | 85.4 ± 4.4 | 78.5 ± 1.5 | | 2 |
| 8 | KHCO$_3$(2 mg)/K$_{222}$$^d$ | 98.9 | 95.5 | | 1 |
| 9 | KHCO$_3$(1 mg)/K$_{222}$$^d$ | 95.5 ± 3.2 | 88.8 ± 1.2 | | 2 |

$^a$TE/trapping efficiency (%) = trapped radioactivity/(trapped + waste).
$^b$RCY/radiochemical yield (%) = isolated/total.
$^c$Acetonitrile (500 µL) is the trapping solvent except for as noted.
$^d$KHCO$_3$ (1 mg)/K$_{222}$ (3.76 mg).

What is claimed is:

1. A method of making [F-18]sulfonyl fluoride without any evaporation step, the method comprising:
   a) passing an aqueous [F-18]fluoride solution or solvent through a solid phase extraction column comprising an anion-exchange resin so that the [F-18]fluoride is trapped on the resin;
   b) rinsing the resin with an organic solvent to eliminate residual water; and
   c) eluting the [F-18]fluoride with an eluting solution to release the [F-18]fluoride from the anion-exchange resin as [F-18]$RSO_2F$ which acts as a source of [F-18] fluoride for a labeling reaction, wherein the eluting solution comprises a compound having the formula $RSO_2R^1$ and an organic solvent, wherein
   R is selected from the group consisting of hydrocarbyl, substituted hydrocarbyl, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heteroaryl, substituted heteroaryl, methyl, trifluoromethyl, and combinations thereof;
   $R^1$ is a leaving group; and
   wherein all method steps are performed with a single peristaltic pump.

2. The method of claim 1, wherein the eluting is done via a circulating method with the single peristaltic pump.

3. The method of claim 1, wherein the single peristaltic pump provides air flow to separate the [F-18]sulfonyl fluoride from the reaction mixture.

4. The method of claim 3, wherein a separator is used to separate the [F-18]sulfonyl fluoride from the reaction mixture using the air flow provided by the pump.

5. The method of claim 4, wherein the separator is selected from an empty cartridge, a vial with needles, and a cartridge with inert materials.

6. The method of claim 1, wherein R is selected from the group consisting of alkyl, substituted alkyl, cycloalkyl, substituted cycloalkyl, aryl, substituted aryl, heteroaryl, substituted heteroaryl, methyl, and trifluoromethyl.

7. The method of claim 1, wherein R is selected from the group consisting of $CH_3$, $CF_3$, $C_6H_5$, $CH_3C_6H_4$, $CF_3C_6H_4$, $NO_2C_6H_4$, $ClC_6H_4$, $FC_6H_4$, $BrC_6H_4$, $IC_6H_4$, $CH_3COC_6H_4$, $MeOC_6H_4$, $CNC_6H_4$, $Me_2NC_6H_4$, $2,4,6-(CH_3)_3C_6H_2$, and $C_5H_5N$ (pyridine).

8. The method of claim 1, wherein $R^1$ is selected from the group consisting of $Cl^-$, $Br^-$, $I^-$, tosylate (TSO), mesylate (MSO), and trifluoromethanesulfate (triflate; TfO).

9. The method of claim 1, wherein $RSO_2$ is selected from the group consisting of tosyl (Ts), mesyl (Ms), trifluoromethanesulfonyl (Tf), nosyl (Ns), besyl (Bs), and N-phenyl-trifluoromethanesulfonimide (NTfPh).

10. The method of claim 1, wherein $RSO_2R^1$ is selected from the group consisting of tosyl chloride, mesyl chloride, trifluoromethanesulfonyl chloride, nosyl chloride, N-Phenyl-bis(trifluoromethanesulfonimide), tosyl anhydride, mesyl anhydride, trifluoromethanesulfonic anhydride, tosyl mesylate, and tosyl triflate.

11. The method of claim 1, wherein the organic solvent is selected from the group consisting of acetonitrile, dimethylformamide, 2-amyl alcohol, tetrahydrofuran, and ethanol.

12. The method of claim 1, wherein the eluting solution further comprises a co-eluting agent selected from the group consisting of $TsOH/TsO^-$, $MsOH/MsO^-$, $TfOH/TfO^-$, $HCl/Cl^-$, $H_2SO_4/HSO_4^-/SO_4^{2-}$, $AcOH/AcO^-$ and $TsOH.H_2O$.

13. The method of claim 1, wherein the anion exchange resin comprises a polymeric matrix and quaternary ammonium groups.

14. The method of claim 1, further comprising regenerating the [F-18]fluoride in the presence of at least one base and at least one phase transfer catalyst during or before a labeling reaction.

15. The method of claim 14, wherein the base is selected from the group consisting of potassium carbonate ($K_2CO_3$), potassium bicarbonate ($KHCO_3$), cesium carbonate ($Cs_2CO_3$), cesium bicarbonate, tetrabutylammonium hydroxide, tetrabutylammonium carbonate, tetrabutylammonium bicarbonate, tetramethylammonium hydroxide, tetramethylammonium carbonate, tetramethylammonium bicarbonate, tetrabutylammonium salts, and tetramethylammonium salts.

16. The method of claim 14, wherein the base and phase transfer catalyst are selected from the group consisting of potassium carbonate/4,7,13,16,21,24-Hexaoxa-1,10-diazabicyclo(8.8.8)hexacosane, potassium bicarbonate/4,7,13,16,21,24-Hexaoxa-1,10-diazabicyclo(8.8.8)hexacosane, potassium carbonate/18-crown-6, and potassium bicarbonate/18-crown-6.

17. The method of claim 16, wherein the base and phase transfer catalyst are pre-dried prior to use.

18. The method of claim 14, wherein regeneration is carried out under anhydrous or aqueous conditions.

19. The method of claim 1, wherein the [F-18]sulfonyl fluoride is used to measure concentration and specific activity of fluoride.

20. The method of claim 1, wherein the eluted solution containing the [F-18]sulfonyl fluoride is used for the synthesis of a PET radiotracer.

* * * * *